(12) United States Patent
Virnig et al.

(10) Patent No.: US 8,343,326 B2
(45) Date of Patent: *Jan. 1, 2013

(54) ACID MIST MITIGATION AGENTS FOR ELECTROLYTE SOLUTIONS

(75) Inventors: Michael Virnig, Tucson, AZ (US); Jack Bender, Corona de Tucson, AZ (US); Louis Rebrovic, North Kingsville, OH (US)

(73) Assignee: BASF Corporation, Florham Park, NJ (US)

( * ) Notice: Subject to any disclaimer, the term of this patent is extended or adjusted under 35 U.S.C. 154(b) by 1217 days.

This patent is subject to a terminal disclaimer.

(21) Appl. No.: 12/166,372

(22) Filed: Jul. 2, 2008

(65) Prior Publication Data

US 2008/0314752 A1 Dec. 25, 2008

Related U.S. Application Data

(63) Continuation-in-part of application No. 11/857,473, filed on Sep. 19, 2007.

(60) Provisional application No. 60/828,389, filed on Oct. 6, 2006.

(51) Int. Cl.
*C25D 21/11* (2006.01)

(52) U.S. Cl. .......................... 205/94; 562/101; 562/103

(58) Field of Classification Search ........................ None
See application file for complete search history.

(56) References Cited

U.S. PATENT DOCUMENTS

| 4,484,990 | A | 11/1984 | Bultman et al. |
| 4,770,814 | A | 9/1988 | Rose et al. |
| 6,833,479 | B2 | 12/2004 | Witschger et al. |

FOREIGN PATENT DOCUMENTS

JP 2007239076 * 9/2007

OTHER PUBLICATIONS

JP 2007-239076 Translation 2007.*
STN abstract of JP 2007-239076; 2007.*
Tjernlund, D. M., et al., "A study of the fire and explosion hazards associated with the electrowinning of copper in Arizona surface mine plants," *Section 8, U.S. Department of Labor, Mine Safety and Health Administration, Investigative Report*, (Mar. 1999).
Cheng, C.Y., et al., "Evaluation of saponins as acid mist suppressants in zinc electrowinning," *Hydrometallurgy*, vol. 73, pp. 133-145 (2004).
Davidsohn, A. S., et al., "Synthetic Detergents," 7th Ed., *LongmanScientific and Technical*, pp. 178-191 (1987).
Kirk-Othmer, "Encyclopedia of Chemical Technology," *John Wiley and Sons*, 3rd Ed., vol. 9, p. 437 (New York 1980).

* cited by examiner

*Primary Examiner* — Yevegeny Valenrod
(74) *Attorney, Agent, or Firm* — Bernard Lau

(57) ABSTRACT

Sulfonate-, sulfate-, or carboxylate-capped, alkoxylated antimisting agents having the structure: $R((AO)_nX)_m((AO)_nH)_p$, and methods of suppressing mist from electrolyte solutions by adding a mist-suppressing amount of one or more compounds selected from the group consisting of compounds of the Formulas $R((AO)_nX)_m((AO)_nH)_p$ and $R^3N^+(CH_3)_2R^4$, and mixtures thereof, to electrolyte solutions.

5 Claims, No Drawings

ACID MIST MITIGATION AGENTS FOR ELECTROLYTE SOLUTIONS

CROSS-REFERENCE TO RELATED APPLICATION

This application is a continuation-in-part of pending U.S. patent application Ser. No. 11/857,473, filed Sep. 19, 2007, which claims the benefit, under 35USC119, of U.S. Provisional Application Ser. No. 60/828,389, filed Oct. 6, 2006, the entire contents of which are incorporated herein by reference.

BACKGROUND OF THE INVENTION

1. Technical Field

This invention relates to the control of mist formation above electrolyte solutions during processes, such as the electrowinning, electroplating, and electroforming of metals, in which a potentially-hazardous mist is formed.

2. Background and Related Art

Electrowinning is the process by which metals are recovered from aqueous electrolyte solutions resulting from the extraction of the metal ion from an acidic or basic leach solution. It is frequently employed in the recovery of metals, such as copper, from the respective metal-containing ores, wherein the leaching, solvent extraction, stripping and electrowinning of metals from their ores have many of the same common unit operations or steps. These steps frequently include: (1) the meted value(s) in the mined and crushed ores being converted to an acid-soluble form, possibly by an oxidizing roast or a reduction; (2) ores from step (1) being leached, such as with an aqueous solution of a strong acid, usually sulfuric acid, to form an aqueous acid leach solution of pH 0.9 to 2.0, containing the desired metal ion and relatively small quantities of other metal ions (impurities that must be removed prior to final recovery of the desired metal(s)); (3) the resulting metal(s)-pregnant aqueous acid leach solution being mixed in tanks (possibly with one or more repetitions in order to improve metal recovery and/or to separate desired metal value(s)) with an extraction reagent, such as an oxime or mixture of oximes, that is/are selective for the desired metal(s), and dissolved in a water-insoluble, water-immiscible organic solvent, to form a metal-extractant complex/chelate that is separated from the metal(s)-depleted aqueous phase in, e.g., a settling tank; (4) the metal-loaded organic phase being then mixed (again, possibly, with one or more repetitions) with a highly-acidic strip solution (e.g., concentrated sulfuric acid), which breaks apart the complex, dissolving the metal ions into another aqueous solution that following another phase separation from the now-metal-depleted organic phase, is customarily forwarded to an electrowinning "tankhouse"; and (5) in the tankhouse, the metal values are deposited on the cathodes by electrodeposition and then recovered from those cathode plates. Other processes may be employed with other metals, such as nickel, zinc, and the like, in order to produce an electrolyte from which their respective metal values may be electrowon.

It is during the electrowinning (electrodeposition) stage that an acidic mist is often generated above the electrolyte (strip aqueous phase). This mist is a result of small bubbles of oxygen being generated at the anode, while the metal is plating out at the cathode, and when these bubbles rise to the top of the electrolyte solution and break, small particles of acidic electrolyte are shot into the air, resulting in an acidic mist.

Electroplating is the process of applying a metallic coating to an article by passing an electric current through an electrolyte in contact with such article. The ASTM adds a quality restriction by defining electroplating as electrodeposition of an adherent metallic coating on an electrode such that a surface, having properties or dimensions different from those of the basic metal, is formed.

In the electroplating process, the metals or metalloids (non-metals that are semiconductors, e.g., arsenic, germanium, and the like, which may be electroplated in the same manner as metals), being used may be present in the aqueous compositions in metallic form and/or in an anionic form, and may be one or more of zinc, nickel, copper, chromium, manganese, iron, cobalt, gallium, germanium, arsenic, selenium, ruthenium, rhodium, palladium, silver, cadmium, indium, tin, lead, bismuth, mercury, antimony, gold, iridium, and/or platinum. In addition, many alloys, such as brass, bronze, many gold alloys, lead-tin, nickel-iron, nickel-cobalt nickel-phosphorous, tin-nickel, tin-zinc, zinc-nickel, zinc-cobalt, and zinc-iron, even lead-indium, nickel-manganese, nickel-tungsten, palladium alloys, silver alloys, and zinc-manganese, are also electroplated commercially.

Another type of electrodeposition in commercial use is a composite form, in which insoluble materials are codeposited along with the electrodeposited metal or alloy to produce particular desirable properties. Polytetrafluoroethylene (PTFE) particles are codeposited with nickel to improve lubricity. Silicon carbide and other hard particles, including diamond, are co-deposited with nickel in order to improve wear properties or to make cutting and grinding tools.

The essential components of an electroplating process are an electrode to be plated (the cathode); a second electrode to complete the circuit (the anode); an electrolyte containing the metal ions to be deposited; and a d-c power source. The electrodes are immersed in the electrolyte, such that the anode is connected to the positive leg of the power supply and the cathode to the negative. As the current is increased from zero, a minimum point is reached where metal plating begins to take place on the cathode.

Plating tanks are formed from materials which are either totally inert to the plating solution or are lined with inert materials in order to protect the tank. For alkaline plating solutions, mild steel materials are used. For acid plating solutions, other materials are used, depending on the chemical composition of the plating bath, such as titanium and various stainless steel alloys, polytetrafluoroethylene, KARBATE® impervious graphite, HASTALLOY® nickel alloys, zirconium alloys, and the like.

The plating tanks are fitted for d-c power, usually with round copper busbars, with filters to remove fine particulate matter. Heating or cooling units may be present, employing heating coils or cooling water coils, and two types of anodes may be used, i.e., soluble or insoluble (when insoluble anodes are used, the pH of the plating solution decreases along with the metal ion concentration, and in some plating baths, a portion of the anodes are replaced with insoluble anodes in order to prevent metal ion buildup or to reduce metal ion concentration). See, e.g., Kirk-Othmer, *Encyclopedia of Chemical Technology*, 4$^{TH}$ Edition, under the heading, "Electroplating".

Because electroplating takes place at the exact molecular surface of a work, it is important that the substrate surface be absolutely clean and receptive to the plating, generally requiring that substrates being electroplated be prepared prior to electroplating. In the effort to get the substrate into this condition, several separate steps may be required, such as soak cleaning, followed by electrocleaning, followed by rinsing.

Formulations of plating baths may be flexible in some systems and very sensitive to variations in others, many of the more recent changes resulting from waste treatment and safety requirements. Besides the ability to deposit a coating having acceptable appearance and physical properties, the desired properties of the plating bath include: high metal solubility, good electrical conductivity, good current efficiencies for anode and cathode, noncorrosivity to substrates, non-fuming, stable, low hazard, low anode dissolution during down-time, good throwing power, good covering power, wide current density plating range, ease of waste treatment, and economical to use. Few formulas have all these attributes, with only a few plating solutions being used commercially without special additives, to brighten, reduce pitting, and/or otherwise modify the character of the deposit or performance of the solution to meet some of the criteria above, with the suppliers of the proprietary additives normally specifying the preferred formulations to be used.

Purification, often needed once a plating bath is prepared, is used periodically to maintain the plating solutions. Alkaline zinc plating solutions are sensitive to a few mg/b of heavy-metal contamination, which may be precipitated using sodium sulfide and subsequently filtered out. Nickel plating solutions may contain excess iron, which may be removed by a process involving peroxide oxidation, precipitation at a pH of about 5, and filtration of the iron. The more complex, less water-soluble organic contaminants, along with some trace metals, are removed with activated carbon treatments in separate treatment tanks. A common purification treatment used both on new and used plating solutions is dummying, in which heavy-metal impurities are removed by electrolyzing before the main electrodeposition step, usually at low current densities, using large disposable steel cathodes, good agitation and lower pH speeding the process. Once the heavy metal impurities have been electroplated onto the disposable steel cathodes, those cathodes are removed and new cathodes are placed into the acid electrolyte so that the electroplating of the desired metal can be performed.

Relatively simple analyses and testing, requiring little equipment are required whenever a new plating solution is made up, and thereafter at periodic intervals. Trace metal contaminants may be analyzed by using spot tests, colorimetrically, and with atomic absorption spectrophotometry. Additives, chemical balance, impurity effects, and many other variables are tested with small plating cells, such as Hull Cells.

The precise makeup of plating bath compositions depends on the metal being plated. For example, cyanide copper plating baths typically contain copper metal, copper cyanide, potassium cyanide, potassium hydroxide, Rochelle salts, and sodium carbonate, while acid copper plating baths (i.e., with sulfuric acid) typically contain copper metal, copper sulfate, sulfuric acid, and various additives, and wants nickel plating baths (with sulfuric acid) typically contain nickel metal, nickel sulfate, nickel chloride, boric acid, and various additives, while sulfamate nickel plating baths contain nickel sulfamate instead of nickel sulfate.

Electroforming is the production or reproduction of articles by electrodeposition upon a permanent or expendable mandrel or mold that is subsequently separated from the electrodeposit, with the electrodeposit becoming the manufactured article. Of all the metals, copper and nickel are the most widely electroformed metals.

A problem common to all of the above electrolysis procedures is the presence of mist-acidic or alkaline-generated above the electrolyte solutions. Such mist is a severe health hazard and causes corrosion of the plant facilities and operating equipment. In order to reduce the quantity of mist, anti-misting agents (also referred to as demisting and mist-suppressing agents) are commonly added to the electrolyte solutions. However, the currently-available anti-misting agents are not completely satisfactory, due to limited demisting ability, high loss rate of such anti-misting agents, interference with the electrolysis process, and/or ecological incompatibilities. In the case of electrowinning, acid mist is particularly noteworthy and troublesome, and the use of mist-suppressing agents can interfere with the related extraction process (e.g., due to partial solubility of these agents in the organic extraction solution, promotion of emulsion formation, promotion of slow phase separation, and interference with extraction or stripping kinetics). In addition, foaming may also be a significant problem.

Tjernlund, D. M., et al., in "A Study of the Fire and Explosion Hazards Associated with the Electrowinning of Copper in Arizona Surface Mine Plants", Section 8, U.S. Department of Labor, Mine Safety and Health Administration, Investigative Report, March 1999, report on the formation of acid mist in electro as follows: "Oxygen bubbles created at the anode rise to the surface of the electrolyte. At the surface, these bubbles [which consist of oxygen surrounded by acid electrolyte] expand above the liquid and then break, releasing entrapped oxygen into the atmosphere. The liquid in the bubble wall just before it breaks is made up of the acid electrolyte solution. As the liquid wall of the bubble ruptures, it disintegrates into extremely small droplets that readily become airborne. The macroscopic effect of this process is to create an acrid acid mist above the cells. This mist readily migrates throughout the workplace and represents a potential health hazard to workers in the tankhouse. It also creates a corrosive atmosphere that can be detrimental to equipment and the tankhouse structure itself." Under Section 8c, "Strategy 4: surfactants", the authors go on: "In most tankhouses, a water-soluble surface tension reducer is used to discourage misting . . . . By lowering the electrolyte surface tension, the gas bubble wall becomes inner when it reaches and protrudes above the electrolyte surface. This causes the bubble to break sooner with less generation of mist droplets".

The authors note further that 3M's FC-100 and FC-1100 FLOURAD™ were commonly-used anti-misting agents. They reported that FC-100 trapped the rising gas in soapsuds-like bubbles above the surface, even at very low concentrations (a few hundred ppm). They note further, however, that the resulting foamy layer also created significant potential fire/explosion problems. They concluded that the FC-1100 surfactant had significantly less tendency to form suds than FC-100, but that, at higher concentrations, it, too, generated an undesirable foam suds layer.

3M states that FC-1100 FLOURAD™ contains 45-55% fluorochemical solids and 45-55% water and provides sulfuric acid mist suppression in the copper electrowinning tankhouse without the formation of a stable foam blanket at the surface of the electrowinning cell. The exact nature of the fluorochemical solid is not disclosed.

C. Y. Cheng et al, "Evaluation of Saponins as Acid Mist Suppressants in Zinc Electrowinning", *Hydrometallurgy*, vol. 73 (2004), pp. 133-145, report on two saponins-rich products (MISTOP® Quillaja saponaria extract and QLZINC®, a commercial licorice product in zinc electrowinning test models) and include the use of MISTOP® saponins in a commercial copper electro operation. The authors report that saponins (high molecular weight glycosides of steroids, steroid alkaloids or triterpenes found in plants, consisting of a sugar moiety linked to a triterpene or steroidal aglycone, often referred to as nonrefined Quillaja extracts) are natural surface-active compounds that give stable foams in aqueous solutions.

U.S. Pat. No. 6,833,479 B2 (Witschger et al, the '479 patent), incorporated herein by reference in its entirety, discloses anti-misting agents that are alkoxy-capped amine and trialkylol compounds having the structure: $R((AO)H)_n H)_m H_p$ (formula (a)), wherein each AO group is, independently, an alkyleneoxy group selected from ethyleneoxy, 1,2-propyleneoxy, 1,2-butyleneoxy, and stryleneoxy groups; n is an integer of from 2 to 100; m is an integer of from 1 to the total number of —OH plus —NH hydrogens in the R group prior to alkoxylation; the sum of m plus p equals the number of —OH plus —NH hydrogens in the R group prior to alkoxylation; and the R group is a group selected from compounds of nine formulas, of which two of them are: $N(CH_2CH_2O)_3$ (b) and $CH_3CH_2C(CH_2O)_3$ (c). Otherwise, the R group of four other formulas represents amine derivatives, as exemplified by formula (b) above; the R group of another formula represents alkoxylated trimethylol-ethane or -propane compounds, as exemplified by formula (c) above; the R group of still another formula represents alkoxylated pentaerythritols; and the final R group alternative represents alkoxylated phenylenediamine.

In testing, however, the monoethanolamine derivative of the particularly-preferred triethanolamines of formula (b) of this reference, when they contain six propylene oxide groups and eleven ethylene oxide groups showed unacceptable interference with the copper electrowinning process, in that, with its use, nodules formed on the necessarily-smooth surface of the cathode. Nodule formation is particularly undesirable, as nodules can grow to the extent that they physically touch the anode, resulting in a direct electrical short in the electrowinning cell, and/or they tend to promote the entrapment of impurities in the copper deposited on the cathode, resulting in poorer quality of the recovered copper.

Additionally, test work carried out with another compound of the '479 patent showed that approximately half of that anti-misting agent was extracted from the aqueous phase into the organic phase during stripping, potentially resulting in a buildup of the surfactant in the organic phase and eventual phase separation problems. The presence of these particular surfactants also adversely affected extraction kinetics. In view of these negative impacts, these types of anti-misting reagents are unacceptable for use in systems involving copper solvent extraction followed by electrowinning.

In addition, U.S. Pat. No. 4,484,990 (Bultman et al) discloses the use of cationic or amphoteric fluoroaliphatic surfactants as anti-misting agents in the electrowinning of metals in an acidic electrolyte, wherein all of these agents contain perfluoroalkyl chains and at least one linking group (e.g., —COO—, —SO$_3$—, —OSO$_3$—, —PO$_{3H}$—, —OPO$_3$H—, or an ammonium group). Functionalized perfluoroalkyl compounds, however, have come under increased scrutiny by the EPA due to their impact on human health and the environment.

Also, U.S. Pat. No. 4,770,814 (Rose et al) discloses the use of amphoteric surfactants containing a long-chain ($C_{13}$-$C_{18}$ hydrocarbons) hydrophobic moiety for the reduction of mist generated by agitation, impact, or spraying, but the use of amphoteric compounds containing hydrocarbon chains, where the chain length is 12 or greater, have been shown to severely impact the solvent extraction/electrowinning circuit by resulting in the formation of a stable emulsion at the organic/aqueous interface.

Extensive research has been devoted to reducing the mist during the electrowinning, electroplating, and electroforming processes, especially in electrowinning processes in which aqueous acidic electrolyte solutions of metal ions are typically used in the electrowinning step. By far the most common solution is to add an anti-misting agent to reduce the mist. However, the currently-available anti-misting agents are not completely satisfactory, there still being a need for improved anti-misting agents that: are ecologically compatible; are effective even at low concentrations; have a low loss rate; are compatible with the other plating bath chemicals and additives; and yet, do not interfere with the kinetics of metal stripping or phase separation in the metal recovery process if the anti-misting agent is present during these steps.

Thus, there still exists a need for improved anti-misting agents for electrolysis/electrodeposition, particularly for use in the electro of copper.

BRIEF SUMMARY OF THE INVENTION

Improved anti-misting agents for the control of mist-acidic or alkaline-generated above electrolyte solutions during the electrowinning, electroplating, and electroforming of metals have been found that are sulfonate-, sulfate-, or carboxylate-capped, alkoxylated compounds of the Formula:

$$R((AO)_n B)_m ((AO)_n H)_p \qquad (I),$$

wherein each AO group is, independently, an alkyleneoxy group selected from ethyleneoxy ("EO"), 1,2-propyleneoxy ("PO"), 1,2-butyleneoxy, and styryleneoxy groups, preferably EO or PO;

n is an integer from 0-to-40, preferably 2-to-30, more preferably 2-to-20, and most preferably 2-to-10;

m is an integer from 1 to the total number of —OH hydrogens in the R group prior to alkoxylation;

p is an integer such that the sum of m plus p equals the number of OH hydrogens in the R group prior to alkoxylation;

B is $SO_3Y$, $(CH_2)_q SO_3 Y$, $CH_2 CHOHCH_2 SO_3 Y$ or $CH_2 CH(CH_3)OSO_3 Y$, where q is an integer from 2-to-4; and Y is a cation, preferably a hydrogen, sodium, potassium or ammonium ion;

R is a group selected from Formulas (II)-(VIII):

$$R^1 C(CH_2O)_3 \qquad (II),$$

where $R^1$ is H, methyl, ethyl, or propyl;

$$C(CH_2O)_4 \qquad (III);$$

$$OC(CH_2O)_2 \qquad (IV);$$

$$N(CH_2CH_2O)_3 \qquad (V);$$

$$(R^2)_x N(CH_2CH_2O)_y \qquad (VI),$$

where $R^2$ is a $C_1$-$C_4$-alkyl, y is 1-3, and x+y=3;

$$O(CH_2)_r O \qquad (VII),$$

where r is 2-to-6; and $$O(CH(CH_3)CH_2)O \qquad (VIII).$$

It will be appreciated by those skilled in the art that the compounds of Formulas (II)-(VIII) of the invention have differing kinds and various numbers of reacted alkyleneoxy moieties (i.e., the AO groups). This is due to the method (i.e., polymerization) by which these compounds are synthesized.

It will be further appreciated by the practitioner that the compounds of Formulas (VI) and (VIII) may be capped at one or both ends. This occurs because the degree of capping is not quantitative and the fully-capped products are not isolated.

In another aspect, the invention includes aqueous electrolyte solutions comprising an amount effective to suppress mist generated above such electrolyte solutions (preferably 2-to-100 ppm, more preferably 2-to-30 ppm) during electrolysis procedures of one or more anti-misting agents of Formula (I) above, in which all variables are as defined above, and/or Formula (IX):

$$R^3N^+(CH_3)_2R^4 \quad (IX),$$

wherein $R^3$ is a group selected from Formulas (X) and (XI):

$$C_6\text{-}C_{12}\text{-alkyl} \quad (X); \text{ and}$$

$$R^5C(O)NH(CH_2)_z \quad (XI),$$

where $R^5$ is a $C_1$-$C_6$-alkyl; and z is 2 or 3; and
$R^4$ is a group selected from Formulas (XII) and (XIII):

$$CH_2CO_2^- \quad (XII); \text{ and}$$

$$CH_2CH(R^6)CH_2SO_3^- \quad (XIII),$$

where $R^6$ is either H or OH.

In a further aspect, the invention includes a method for reducing misting in electrolyte solutions containing metal ions by adding thereto a mist-suppressing quantity of one or more of the anti-misting agents of Formulas (I) and/or (IX) above, in which all variables are as defined above.

DETAILED DESCRIPTION OF THE INVENTION

Other than where otherwise indicated or understood, all numbers expressing quantities of ingredients or reaction conditions used herein are to be understood as modified in all instances by the term "about". In addition, it is understood that the term "metals" also includes metalloids.

In Formula (I) above, compounds that are fully alkoxylated are preferred.

In Formula (II), when $R^1$ is methyl or ethyl, and in Formula (V), m is preferably 1.5 to 3, more preferably 2 to 3.

The styryleneoxy groups may be unsubstituted, or may contain substituents on the phenyl group, such as one or more $C_1$-$C_6$-alkyl groups, $C_1$-$C_6$-alkoxy groups, and/or other groups that will not interfere with electrolysis.

The compounds of Formula (II), in which $R^1$ is methyl or ethyl, i.e., sulfonate- or sulfate-capped, alkoxylated trimethylol-ethane or -propane compounds, are preferred compounds of the invention. Such compounds, in which AO is EO or PO, are preferred, and those in which AO is EO are more preferred. Most preferred are the propane derivatives of Formula (II), in which $R^1$ is ethyl.

Electrolyte solutions containing, and methods of reducing misting in electrolyte solutions by adding, either alone or in a mixture with one or more compounds of Formula (I), one or more compounds of Formula (IX), in which $R^3$ is represented by Formula (XI), $R^5$ is preferably $C_3$-$C_6$ alkyl, and z is preferably 2 to 3, more preferably 3, as well as those in which the $R^3$ group is represented by Formula (X), where $R^3$ is hexyl, octyl, an octyl/decyl mixture, or decyl, and where the $R^4$ group is represented by Formula (XII), are preferred.

The above alkoxylated compounds may be readily produced by alkoxylating the corresponding alcohols and/or amines by methods well known to those skilled in the a e.g., by reacting the alcohols and/or amines with the desired quantities of alkylene oxides.

The compounds in Formula (IX), in which the $R^3$ group is represented by Formula (X), where $R^3$ is decyl, and where the $R^4$ group is represented by Formula (XII), may be readily produced by reacting a N,N-dimethyl tertiary amine with either 1,3-propanesultone or with sodium chloroacetate, according to standard techniques described in the literature.

The anti-misting agents—the novel compounds and/or the compounds not previously known to be useful as anti-misting agents—according to this invention are useful in reducing or minimizing the misting problems that may be present in electrowinning compositions, electroplating compositions, and/or electroforming compositions and/or in procedures that utilize aqueous electrolyte solutions of metals ions or aqueous electrolyte dispersions of metals in metallic form, as well as with waste solutions containing dissolved metals. In all cases, it being understood that the metals/metalloids may be present in ionic form and/or in elementary form. And in the electrolysis of metals from aqueous electrolyte solutions containing the metal(s) to be captured the utility of the compounds according to the present invention is not dependent on the particular metal(s) present in the electrolyte solutions.

The anti-misting agents of the present invention are effective in quantities as low as a few parts per million, based on the electrolyte composition, e.g., from 2-to-100 ppm, preferably from 2-to-30 ppm, and most preferably from 5-to-25 ppm. In an electrowinning application, they may be added to the aqueous strip solution used in the stripping stage following the solvent extraction stage, or to the metal-pregnant aqueous solution that results from the stripping of the organic phase in the stripping stage, or, preferably, to the metal-containing electrolyte/strip aqueous phase in the electrowinning tankhouse.

There are a number of electroplating methods for which the demisting agents of the invention may be used. Materials, such as strip steel, may be plated in plating tanks where coils of steel are unrolled in a continuous basis, fed through a series of preparation steps, and then into the plating tank. Wire that is uncoiled from the spools or reels on which it was wound, may be passed through various processing steps and then plated, with metals, such as copper, copper alloys, zinc, iron, iron alloys, nickel, nickel alloys, gold, or silver, as individual strands. Stampings, moldings, and castings are typically mounted onto specially-designed plating racks for electroplating. Small parts, e.g., dipping baskets and plating barrels made of inert plastic materials, may be electroplated using bulk plating methods. Where parts are large and only smaller areas of the parts are to be plated, brush plating is used, i.e., using plating tools which are shaped anode materials covered with an absorbent material saturated with the plating solution.

Insoluble anodes are used exclusively in the plating baths of the present invention. Chromium plating solutions utilize lead-tin, lead-antimony, or just lead anodes; gold and other precious metal plating processes use stainless steel anodes, keeping inventory costs down.

However, the use of insoluble anodes may, unfortunately, also result in side effects. In alkaline cyanide solutions, the generation and buildup of carbonates is accelerated as a result of the use of insoluble anodes, along with a significant reduction in alkalinity. In acidic solutions, the pH decreases, requiring frequent adjustments. In sulfamate nickel plating solutions, insoluble anodes, and even slightly passive soluble anodes, partially oxidize the sulfamate ion to form sulfur-bearing compounds which change the character and performance of the deposit. (See Kirk-Othmer, supra).

Production of the Compounds of the Invention

The synthesis of the sulfoalkyl derivatives of the compound of Formula I (i.e., those in which $B\!=\!(CH_2)_q SO_3 Y$) may typically be accomplished as a two-step reaction that may be performed in the same reaction vessel. The first step of the reaction involves the addition of sodium metal to the alkoxylated polyol (i.e., one of the compounds from Formula (II)-(VI)) to form the corresponding terminal sodium alkoxide. The second step of the reaction is the addition of 1,3-propane sultone to the sodium alkoxide formed in the first step. Toluene (or other inert organic solvent) is used as the solvent throughout the process.

The sulfonate-capped derivatives of the compounds of Formula (I) in which B=$CH_2CHOHCH_2SO_3Y$ (2-hydroxypropanesulfonate) may also typically be accomplished as a two-step reaction (known as a Williamson synthesis) that may be performed in the same reaction vessel, preferably in an inert organic solvent, such as toluene. The first step of the reaction involves the addition of sodium metal to the alkoxylated polyol (i.e., one of the compounds from Formula (II)-(VI)), as above, in order to form the corresponding terminal sodium alkoxide. The second step of the reaction is the addition of 3-chloro-2-hydroxy-1-propanesulfonic acid sodium salt to the sodium alkoxide formed in the first step, and the product is recovered by addition of water to the organic phase after cooling. The aqueous phase is then isolated.

The production of the sulfate-capped derivatives of the compounds of Formula (I), in which B=$SO_3Y$, may be accomplished by starting with the same ethoxylated polyols (i.e., one of the compounds from Formula (II)-(VI)) described above and converting their terminal hydroxyl groups to sulfates by reactions known in the art. Alternatively, the terminal hydroxyl may be capped by reacting them with allyl chloride, and then adding sulfuric acid across the double bond to give a slightly different type of sulfate cap.

The alkoxylated compounds of Formula (I) above, may be readily prepared by alkoxylating the corresponding alcohols and/or amines by methods well known to those skilled in the am e.g., by reacting the alcohols and/or amines with the desired quantities of alkylene oxides. Such syntheses are illustrated and/or exemplified in *Synthetic Detergents*, A. S. Davidsohn and B. Milwidsky, Seventh Edition, LongmanScientific and Technical, 1987, pp. 178-191, and Kirk-Othmer, *Encyclopedia of Chemical Technology*, 3$^{rd}$ Edition, Volume 9, John Wiley and Sons, New York, 1980, p. 437, among other places.

The compounds of Formula (IX) are classified as betaines. The compounds, in which the $R^3$ group is represented by Formula (XI) and the $R^4$ group is represented by Formula (XIII), are called sulfobetaines betaines. Such compounds, where z=3, are called 3-[(3-akylamino-propyl)-N,N-dimethylammonio]-propane sulfontes or 2-hydroxy-3-[(3-alkylamino-propyl)-N,N-dimethylammonio]-propane sulfonates (if the $R^5$ group is $C_1$, then replace "alkyl" with "methyl"; if the $R^5$ group is $C_2$, then replace "alkyl" with "ethyl"; if the $R^5$ group is $C_3$, then replace "alkyl" with "propyl", and so on) The first step in the synthesis in both cases is the reaction of 3-(dimethylamino)propyl amine with an ester under standard transamidification conditions to generate the corresponding amide. In the second step, the resulting amide is reacted with either the 1,3-propane sultone or 2-hydroxy-3-chloropropanesulfonic acid under conditions known in the art.

The compounds of Formula (IX), in which the $R^3$ group is represented by Formula (X) and the $R^4$ group is represented by Formula (XIII), are classified as all N,N-dimethylsulfonates. The synthesis of the compounds is accomplished by the reaction of 1,3-propane sultone or 2-hydroxy-3-chloropropanesulfonic acid with a N-alkyl-N,N-dimethyl amine in anhydrous acetone using, conditions known in the art.

These compounds of Formula (IX), in which the $R^3$ group is represented by Formula (X) and the $R^4$ group is represented by Formula (XII), are classified as alkyl N,N-dimethylglycines. The synthesis of the compounds is accomplished by the reaction of sodium chloroacetate with a N-alkyl-N,N-dimethyl amine in water. After the reaction is complete, there is no need to further purify of the product.

The invention is further illustrated, but not limited, by the following Examples, the compounds for which were prepared by first reacting ethylene oxide with triethanolamine, then reacting the resulting product with 1,2-propylene oxide.

EXAMPLE 1

Preparation of Sodium Sulfopropyl Etherate of Ethoxylated 2-ethyl-2-(hydroxymethyl)propane-1,3-diol (Compound A)

To a 5000 mL round bottom flask equipped with a Dean-Stark trap/condenser/drying tube, a mechanical sire, and a pressure-equalizing funnel, was added 199.5 g (0.45 mol) trimethylolpropane that has reacted with seven moles of ethylene oxide and 2.75-3 L of toluene. The solution was refluxed for four hours to remove any water (azeotrope using the Dean-Stark trap). The Dean-Stark trap was then removed, and the condenser was replaced with a dry condenser. The temperature of the reaction flask was kept at just the refluxing temperature of toluene (overheating causes the solution to darken considerably). To the reaction flask was then added 31.05 g (1.35 mol, 1 mol equivalents to the hydroxyl groups of the trimethylolpropane containing seven ethyleneoxy groups) of sodium metal, washed with hexane prior to use, over a one hour period. Addition of the sodium metal resulted in a substantial increase in temperature. The solution was then stirred for four additional hours. While there was some sodium still in the reaction vessel, it was completely consumed in the next phase of the reaction.

1,3-Propane sultone (165.0 g, 1.35 mol) was transferred to the addition funnel along with 400 mL of toluene. The addition of the 1,3-propane sultone was performed over a 20-30 minute period. Addition of the 1,3-propane sultone was carefully monitored because of the extreme temperature increase at the beginning of the addition, and the formation of an intractable solid at the end of the addition. The solution was stirred as the 1,3-propane sultone was added and continued to be sired until the formation of the solid product caused the mechanical stirrer to stop, then the toluene was decanted off while still hot. To remove the solid, the contents of the flask had to be dried using a vacuum pump and the solid broken apart with a steel rod. The solid was collected, crushed, and washed with hot toluene. The crushed solid was dried using a vacuum of 500 millitorr, and was pulverized using a mortar and pestle. The yields from tree runs of this preparation were 95.45%, 91.37%, and 97.8% respectively (this preparation is typical for Formula I compounds).

Preparation of N-Decyl-N,N-dimethylglycine (Compound E)

The following is a typical reaction for the synthesis of the alkyl N,N-dimethylglycines. To a 500 mL flask 3 necked flask equipped with a condenser, a mechanical stirrer, and the other opening sealed with a teflon stopper was added 92.70 g N-decyl-N,N-dimethyl amine (0.50 mol) and 58.25 g sodium choloroacetate (0.50 mol) dissolved in 151.0 g of water. The solution was heated to 90° C. using a silicon oil bath. The temperature was kept constant throughout the reaction using a temperature probe connected to the hotplate. The sting rate was kept at 250 rpm throughout the reaction. After tree hours a sample was taken and potentiometrically titrated with 0.1 M NaOH using standard techniques. Since there was no free amine present (<1%) the reaction was terminated. The yield from the reaction was quantitative. (this preparation is typical for alkyl N,N-dimethylglycines.)

EXAMPLE 2

Anti-Misting Capability

In order to demonstrate the anti-misting characteristics of these products, two compounds of the invention: the tri-sodium sulfopropyl ether of trimethylolpropane containing seven ethyleneoxy groups (Compound A) and the tri-sodium sulfopropyl ether of triethanolamine containing six polyoxypropylene groups and eleven polyoxyethylene groups (Compound B) were tested against five hundred mL samples of copper electrolyte solution (50 g/l $Cu^{+2}$, 0.2 g/l $Co^{+2}$, 1.5 g/l $Fe^{+3}$, 170 g/l sulfuric acid) in a jacketed beaker controlled at 45° C., with mist being generated by passing air through a fine frit (4-8 micron) scintered glass bubbler in the copper electrolyte. The mist was sampled by suctioning air through a sampling tube 1.5 inches above the liquid level, the tube being connected to a water trap. At timed intervals, the water from the trap was titrated with sodium hydroxide to a bromphenol blue endpoint to determine the amount of acid contained therein, the results in the Table being calculated in millimoles of sulfuric acid captured per hour. The results of the anti-misting tests are shown in Table 1:

TABLE 1

| | Anti-Misting | |
|---|---|---|
| Concentration (ppm) | Compound A (mmol $H_2SO_4$/hr) | Compound B (mmol $H_2SO_4$/hr) |
| 0 | 3.44 | 3.26 |
| 5 | 0.90 | 0.77 |
| 10 | 0.59 | 0.38 |
| 20 | 0.39 | 0.23 |
| 30 | 0.23 | 0.16 |
| 40 | 0.20 | 0.14 |

These results demonstrate that Compounds A and B of the invention substantially reduce the level of mist to commercially-acceptable concentrations.

EXAMPLE 3

Conner Electrowinning Comparison

Three anti-misting agents according to the invention (Compound A [from Example 2, where m is ~3], the sodium sulfopropyl ether of monoethanolamine containing six propylene oxide groups and eleven ethylene oxide groups, where m is ~3 [Compound C] and monoethanolamine containing six propylene oxide groups and eleven ethylene oxide groups reacted with only two moles of propane sultone for each mole of the monoethanolamine, where m is ~2 [Compound D]) and monoethanolamine contacted with six moles of propylene oxide and eleven moles of ethylene oxide (Compound 1, the preferred embodiment from U.S. Pat. No. 6,843,479), and a blank run with no anti-misting agents, were tested in an electrowinning apparatus with guar added as a smoothing agent. The basis for all three new molecules is either Compound 1 or trimethylolpropane containing seven ethyleneoxy groups. The free anti-misting agents according to the invention tested were:

The results demonstrated that Compound A provided a clean, even plate. The plate of Compound B was almost as good quality as that of Compound A. However, the plate of Compound C showed that it had a slight tendency to form nodules. Earlier testing demonstrated that the plate for Compound 1 contained substantial nodule growth which not only results in a poor plate quality for copper recovery, but also can produce hazardous electrical conditions in the cell.

Procedure

For each 16-hour run, 35 L of electrolyte was prepared with concentrations of 38 g/l Cu, 2 g/l $Fe^{3+}$, 0.1 g/l Co, 0.01 g/l Cl, and 175 g/l $H_2SO_4$. This was accomplished by dissolving appropriate levels of $CuSO_4$, $Fe_2(SO_4)_3$, $CoSO_4$, NaCl, and $H_2SO_4$ in deionized water. Each solution was then split into two 5-gal buckets to feed the electrowinning for two days at eight hours each day.

An electrowinning cell, housing one cathode and two anodes, was made from PVC plastic and fitted with a water jacket in order that the cell could be maintained at a given temperature. The cathodes were cut from stainless steel with a surface plating area of about 3 in×3 in (0.0625 ft² counting both sides) and a thickness of slightly less than one-sixteenth inch; the anodes were lead plates and slightly smaller in width and height than the cathode. The electrolyte in the cell, while running, measured 11 cm deep×8 cm wide×12.5 cm long, for a volume of 1.1 L, and it was pumped into and out of the cell at a rate of 28 ml/min, in order to achieve a 3 g/L drop in Cu concentration across the cell. The current density used in the experiments was 30 A/ft² (within the typical tankhouse current densities of between 12 and 38 A/ft²), and based on the surface area of the cathode, the current needed to flow to the cell was calculated to be 3.75 A.

At the beg of each test, 0.07 g (4 ppm) of Galactasol® 40H4CD guar gum derivative and 0.175 g (10 ppm) of the potential demisting agent for that run were added, while stirring with an impeller, to one of the two buckets containing the electrolyte. The jacket for the electrowinning cell was filled with deionized water and hooked up to a recirculating water bath in order to maintain the electrolyte in the cell at 45° C. The inlet tube for the cell was run through a peristaltic pump set to 28 ml/min and placed into the bucket containing the spiked electrolyte, which had been warmed up on a hot plate to ~45° C., with the exit tube being placed in a clean, empty 5-gal bucket. The 1200 ml of warm electrolyte was added to the cell to fill it to the appropriate level (in order that the submerged area of the cathode was 0.0625 ft²). The anode and cathode were hooked up to a constant current power supply, and the pump was turned on. Once the lines were full and the electrolyte was flowing through the cell, the power supply was turned on and set to 3.75A continuous current.

This arrangement was run for eight hours before turning off the power supply, the water bath supplying the jacket and the peristaltic pump, and the wire to the cathode from the power supply was unhooked in order to prevent current backflow. After allowing the cathode to sit in the bath overnight, the cathode was dried, weighed, and photographs were taken of it.

The above procedure was repeated the following day with the second batch of tests solutions. Again, after allowing the cathode to sit in the bath overnight, the cathode was dried, weighed, and photographs were taken of it.

The electrowinning tests for Compound A and Compound D (Compound C was not checked) were repeated in a 40-hour run in order to ensure no obvious negative characteristics of the copper deposit Each 40-hour run required 70 L of electrolyte, split into five 14-L batches, each batch receiving 0.056 g (4 ppm) of the guar polymer and 0.14 g (10 ppm) of the demisting agent being evaluated. These runs confirmed that Compound A produces high quality plates and Compound D tends to produce plates having a limited number of small nodules.

EXAMPLE 4

Effect on Copper Extraction Circuit Kinetics

The extraction circuit kinetics tests were run using the Cognis standard quality control test method in order to determine whether the tested anti-misting agents were too soluble in the organic phase or have an adverse effect on phase separation in the extraction stripping phase.

A 4-L batch of 10 v/v % LIX® 984N mixed ketoxime/aldoxime extraction reagents was made up in Conoco® 170Exempt aliphatic diluent. One-liter of Cognis QC Electrolyte (i.e. solution contains 35±0.7 g/l Cu (as the sulfate) and 160±2 g/l $H_2SO_4$) batches (six in total) were spiked to levels of 20 and 50 ppm (three with 20; three with 50), respectively, with each of Compounds A, C and D (from Example 3). One liter of QC Electrolyte, without any demisting agent, was run rough the QC Test as a control batch. A 400-ml sample of the LAX 984N reagent solution was contacted with 400 ml of one of the electrolyte solutions for 3 minutes by shaking vigorously in a 1-L separatory funnel. The solutions were allowed to separate, a sample of the equilibrated organic (E.O.) was taken, and 350 ml of the organic was placed in a 1-L baffled beaker. An impeller was lowered into the organic solution in order that the top of the polypropylene hub of the impeller was at the surface level of the organic. The impeller was started up at 1750 rpm and 350 ml of a control feed (6.0 g/l Cu, 3.0 g/l $Fe^{+3}$, pH=2.0) was added over five seconds. A sample of the emulsion was taken at 30 seconds to obtain a sample of the organic (E30). The mixing continued for 300 seconds total at which time the mixer was stopped. The time required for a complete separation of the phases was then determined phase break time). A sample of the organic after 300 seconds of mixing (E300) was then taken. The organic and aqueous phases were transferred to a 1-L separatory funnel and allowed to separate again. A 325-ml sample of that organic was placed in a 1-L baffled beaker and a clean impeller was placed at the same level as the extraction test. The impeller was started up at 1750 rpm and 325 ml of the same QC Electrolyte as the first contact was added over 5 seconds. A sample of the emulsion was taken at 30 seconds to obtain a sample of the organic (S30). The mixing continued for 300 seconds total, at which time the mixer was stopped, and the phase break time was then determined. A sample of the organic phase was then taken (S300), with the results for the seven kinetics tests shown in Table 1.

TABLE 2

Kinetics Test Results

|  | Assay | E.O. | E30 | E300 | S30 | S300 | Phase Break (s) |
|---|---|---|---|---|---|---|---|
| Blank | Cu | 1.42 | 4.72 | 4.75 | 1.64 | 1.63 | 95, 75 |
|  | % E300 |  | 99.10% |  | 99.68% |  |  |
| 20 ppm | Cu | 1.44 | 4.70 | 4.73 | 1.65 | 1.63 | 90, 55 |
| Cmpd. C | % E300 |  | 99.09% |  | 99.35% |  |  |
| 50 ppm | Cu | 1.45 | 4.71 | 4.76 | 1.68 | 1.64 | 90, 110 |
| Cmpd. C | % E300 |  | 98.49% |  | 98.72% |  |  |
| 20 ppm | Cu | 1.43 | 4.69 | 4.73 | 1.64 | 1.63 | 85, 80 |
| Cmpd. A | % E300 |  | 98.79% |  | 99.68% |  |  |
| 50 ppm | Cu | 1.42 | 4.69 | 4.72 | 1.65 | 1.63 | 95, 75 |
| Cmpd. A | % E300 |  | 99.09% |  | 99.35% |  |  |
| 20 ppm | Cu | 1.41 | 4.66 | 4.71 | 1.64 | 1.62 | 145, 95 |
| Cmpd. D | % E300 |  | 98.48% |  | 99.35% |  |  |
| 50 ppm | Cu | 1.42 | 4.66 | 4.74 | 1.68 | 1.62 | 120, 150 |
| Cmpd D | % E300 |  | 97.59% |  | 98.08% |  |  |

The above extraction circuit kinetics data demonstrates that Compound A and Compound C do not have any substantial impact on the solvent exaction performance. However, Compound D does appear to have a small negative impact on phase separation.

EXAMPLE 5

Surface Tension Determinations

Surface tensions were measured on QC Electrolyte with Compounds A, C and D, FC1100, and Mistop at levels of 5, 10, 20, and 40 ppm. The results are shown in Table 3.

TABLE 3

Surface Tension Determinations

| Mist Suppressant Concentration | Surface Tension (dynes/cm) | | | | |
|---|---|---|---|---|---|
| (ppm) | Cmpd. C | Cmpd. A | Cmpd. D | FC1100 | Mistop |
| 0 | 76.7 | 76.7 | 76.7 | 76.7 | 76.7 |
| 1 | — | 63.7 | 60.7 | 53.7 | 64.6 |
| 5 | 64.4 | 61.6 | 62.4 | 58.5 | 62.0 |
| 10 | 61.5 | 59.8 | 61.8 | 61.4 | 58.3 |
| 20 | 62.4 | 63.5 | 59.9 | 59.5 | 61.7 |
| 40 | 60.0 | 54.7 | 58.0 | 54.3 | 59.5 |

Based on the above surface tension comparisons, Compounds A, B, and C are equally effective in lowering the surface tension of the electrolyte as the commercially-accepted FC1100.

EXAMPLE 6

Surface Tension Measurements of Compounds of Formula (IX)

Surface tension measurement of QC electrolyte containing various concentrations of anti-misting agents were performed as the reduction in surface tension is a good indicator of mist suppression behavior. These measurements were carried out utilizing a Fisher Surface Tensiomat 21 in manual mode utilizing the du Nouy methodology (standard method). Results for the most preferred compounds of the invention may be found in Table 1; Compound E (N-decyl-N,N-dimethylglycine), Compound F (N-octyl-N,N-dimethylglycine), Compound G N-dodecyl-N,N-dimethylglycine). FC-1100, from 3M, is the commercially accepted anti-misting agent.

TABLE 1

Surface Tension Determinations

| Mist Suppressant | Surface Tension (dynes/cm) | | | |
|---|---|---|---|---|
| Concentration (ppm) | Cmpd. E | Cmpd. F | Cmpd. G | FC-1100 |
| 0 | 62.0 | 63.5 | 61.3 | 61.3 |
| 10 | 46.4 | 49.4 | 41.2 | 42.0 |
| 20 | 43.2 | 46.5 | 40.9 | 40.7 |
| 30 | 41.1 | 43.7 | 40.5 | 40.8 |
| 40 | 39.9 | 43.2 | 39.9 | 39.3 |
| 50 | 39.5 | 41.9 | 39.4 | 37.0 |

EXAMPLE 7

Anti-Misting Capability of Compounds of Formula (X)

In order to measure acid mist suppression of anti-misting agents of Formula (IX), these compounds were added to an operating electrowinning cell. The electrolytic cell was made of 3/16" thick Lexan plastic and measured 3.5" in width, 8.5" in length, and 6.5" in depth. An overflow weir was placed near the exit side of the cell and measures five inches in height. An entrance baffle, also 5" in length, was placed near the electrolyte entrance. Along the top of the cell, nine square-cut grooves were cut to allow the anode and cathode busbars to sit on cell, Centered 0.5" beneath the 4$^{th}$ groove cut, a 5/16" hole was bored out to serve as a sample port. Two 0.5" holes were bored in the opposite ends of the cell to serve as feed entrance and exits. The entrance hole was bored at 4.25" from the bottom of the cell, and the exit hole was bored at 2.5" above the bottom of the cell. Teflon-taped fittings were screwed into the ends to provide for tubing attachments.

Anodes and cathodes were cut in order to fit the electrowinning cell. Lead anodes were cut from 1/16" thick lead sheet and measure 3"×5.25". The anodes were attached to a copper busbar with two small threaded screws and 12 Gauge copper wire was run between the two anodes in series. The last anode was connected with 12 Gauge copper wire to the positive terminal of the DC power supply. Cathodes were made from 1/16" thick stainless steel 316 (SS316), and had the same dimensions as the anodes. Similarly to the anode, the cathode was attached to a copper busbar with a threaded screw with 12 Gauge copper wire connections between cathodes. The busbar was connected to the negative terminal on the DC power supply.

The collection of acid mist was accomplished by drawing the mist through a reservoir of water in an Erlenmeyer flask at a constant flow rate (1800 mL/min trough a 1/16" inlet nozzle). After a timed interval, the water from the reservoir was titrated with a standardized sodium hydroxide solution to a phenolphthalein endpoint. The amount of sodium hydroxide used in the titration was then used to determine the relative amount of acid mist.

Procedure:

Copper electrolyte was prepared in 40 L batches and included: 35 g/l Cu, 2 g/l Fe$^{3+}$ and 1780 g/l H$_2$SO$_4$. This was done by dissolving appropriate levels of CuSO$_4$, Fe$_2$(SO$_4$)$_3$, and H$_2$SO$_4$ in deionized water. Analysis of the solution was performed prior to running by AAS. Approximately 15 ppm of GALACTASOL® 40H4CD guar solution was added to the electrolyte for cathode smoothing purposes. An anti-misting agent was then added at the appropriate concentration, and the entire solution was thoroughly mixed prior to introduction into the EW cell.

The electrolyte was introduced into the electrolytic cell at a flow rate of 30 mL/min via a peristaltic pump. The electrolyte reservoir was placed in a re-circulating water bath in order to control the temperature to between 40° C. and 42° C. A stir bar was placed in the electrolytic cell to ensure proper mixing. Once the electrolyte had reached 40° C., the DC power was turned on and voltage and amperage adjusted to give 4.10 A at 5.0 to 5.2 V. This should provide a current density of ~300 A/m$^2$, in a single-cathode arrangement. The electrolytic reaction was allowed to proceed for three hours.

After three hours, the sample probe and tubing were rinsed with a few aliquots of DI water into the water trap to qualitatively transfer any residual acid on the interior surfaces of the probe and tubing. A few drops of phenolphthalein were added to the water in the Erlenmeyer flask. The acid mist/water sample was then titrated with standardized 0.1 M NaOH. The endpoint of the titration is indicated by a change in color of the solution from clear to pink. The amount of NaOH is proportional to the acid mist generated and the results of the analysis are shown in Table 2 for the most preferred betaines (Compounds E, F, and G).

TABLE 2

| Mist Suppression Determinations | | | | |
|---|---|---|---|---|
| Mist Suppressant | Acid Mist (mL of 0.1M NaOH titrant) | | | |
| Concentration (ppm) | Cmpd. E | Cmpd. F | Cmpd. G | FC-1100 |
| 0 | 5.06 | 4.98 | 5.06 | 5.06 |
| 10 | 2.44 | 3.66 | 2.32 | 1.82 |
| 20 | 2.21 | 3.04 | 2.15 | 1.67 |
| 30 | 1.96 | 2.46 | 1.90 | 1.71 |
| 40 | 1.94 | 2.28 | 1.35 | 1.76 |
| 50 | NA | 2.42 | 0.58 | 0.40 |

Mist values for the 40 and 50 ppm concentrations of Compound G in Table 2 were very low due to foaming on the surface of the electrowinning solution. At no other time was any foaming noticed for the other compounds in the electrowinning trials at concentrations up to 100 ppm.

EXAMPLE 8

Effect of Anti-Misting Agent on Extraction Circuit Kinetics of Compounds of Formula (IX)

Extraction circuit kinetics were obtained using a two extraction/one strip stage (2E/1S) circuit in order to determine whether the Anti-misting agents had a negative effect on the organic phase or the phase separation times. The countercurrent 2E/1S system was comprised of Lexan mix boxes (180 mL capacity), each containing an impeller mixer which agitates the solution in the mix-box portion of the stage. The residence time of the cell was 180 seconds. The impellers were run at 1750 rpm and the continuity of the system was kept organic continuous.

Initial levels of pregnant leach solution (PLS), strip electrolyte (SE), and loaded organic (LO) were added to the appropriate mix boxes. An initial equilibrium was established with the organic by pre-contacting fresh organic reagent with strip electrolyte prior to addition into the circuit. PLS was fed into the system at a rate of 15 mL/min. Organic (either 10% v/v or 30% v/v LIX® 984N in Shellsol D70) was pumped from an overflow surge tank into the circuit at a rate of 30 mL/min. Strip electrolyte was also pumped in at a rate of 30 mL/min. All circuit stages were kept at ambient temperature with the exception of the strip stage. The strip stage was heated to between 40° and 42° C. The circuit was run for a minimum of 24 hours of operation.

Synthetic electrolyte (~35 g/L Cu, 2 g/L Fe$^{3+}$, 180 g/L H$_2$SO$_4$, 15 ppm guar) was pre-dosed with a specific concentration of mist suppressant. As this solution was run through the circuit, samples were taken to determine if there were any issues with kinetics or circuit metallurgy. Overall organic entrainment and phase-break times were determined for the two LIX® 984N concentrations (10% and 30%). Samples were taken after approximately 24 hours of total circuit run time and analyzed for metal concentrations in the various circuit operations (Strip, E1, E2, Raffinate streams). The results of the analysis may be found in Table 3.

The only negative impact on solvent extraction by the most preferred anti-misting agents (Compounds E, F, and G) occurred when using Compound G. At low concentration (10 ppm), Compound G was noted to cause a stable emulsion layer to form in the strip stage. This emulsion layer did not break and was stable for well over 24 hours, filling the settler box nearly to its full depth. No emulsion layers were noted with Compounds E or F at any dosage concentration. Entrainments for Compounds E or F were in the 100-300 ppm range, which is consistent with industrial levels. All other results in Table 3 are consistent with normal operating values.

TABLE 3

| | Circuit Results | | | | | | | | | |
|---|---|---|---|---|---|---|---|---|---|---|
| Circuit | 10% LIX ® 984N 30 ppm Cmpd E | | 30% LIX ® 984N 30 ppm Cmpd E | | 10% LIX ® 984N 30 ppm Cmpd F | | 30% LIX ® 984N 30 ppm Cmpd F | | 10% LIX ® 984N 10 ppm Cmpd G | |
| Operation | Cu (g/L) | Fe (ppm) | Cu (g/L) | Fe (ppm) | Cu (g/L) | Fe (ppm) | Cu (g/L) | Fe (ppm) | Cu (g/L) | Fe (ppm) |
| E1 | 3.11 | 1.40 | 7.79 | 8.68 | 3.17 | 1.70 | 7.55 | 10.81 | 3.11 | 1.40 |
| E2 | 1.60 | 2.90 | 5.05 | 7.02 | 1.56 | 3.00 | 5.05 | 7.97 | | |
| S1 | 1.52 | 0.28 | 4.92 | 0.62 | 1.47 | 0.30 | 4.82 | 0.84 | | |
| Feed | 3.08 | 2.40 | 7.91 | 8.84 | 3.16 | 2.20 | 8.01 | 10.14 | 3.13 | 2.30 |
| Raffinate | 0.09 | 3.01 | 0.12 | 3.12 | 0.10 | 3.63 | 0.11 | 3.43 | 0.12 | 3.33 |
| Rich Electrolyte | 39.69 | 2.02 | 40.12 | 2.31 | 38.42 | 2.33 | 39.54 | 2.81 | | |
| Lean Electrolyte | 36.61 | 1.95 | 35.96 | 1.86 | 36.20 | 2.22 | 36.76 | 2.06 | | |
| PLS | 1.39 | 2.98 | 1.41 | 1.41 | 1.39 | 2.98 | 1.41 | 1.41 | 1.37 | 2.87 |
| Aqeous Break | 53 sec | | 64 sec | | 48 sec | | 74 sec | | 75 sec | |
| Organic Break | 68 sec | | 89 sec | | 73 sec | | 80 sec | | >300 sec | |
| Entrainment | 137 ppm | | 317 ppm | | 167 ppm | | 334 ppm | | NA | |

EXAMPLE 9

Copper Quality of Compounds of Formula (IX)

Copper was plated for 8-22 hours using the same conditions as described in Example 1 in order to inspect the quality of the copper deposited. The quality of the cathode was determined by a visual inspection using microscopy at low power (approximately 125× magnifications). The cathode produced using Compounds F, F, 6 and FC-1100 was of high quality and had essentially smooth plates with little to no nodulation.

What is claimed is:

1. A method for reducing misting from electrolyte solutions containing at least one metal in ionic or dispersed metallic form, the method comprising adding thereto a mist-suppressing quantity of one or more of the compounds selected from the group consisting of compounds of Formula (I), compounds of Formula (IX), and mixtures thereof:

$$R((AO)_n B)_m ((AO)_n H)_p \quad (I)$$

and $$R^3 N^+(CH_3)_2 R^4 \quad (IX),$$

wherein
each AO group is, independently, an alkyleneoxy group selected from ethyleneoxy, 1,2-propyleneoxy, 1,2-butyleneoxy, and styryleneoxy groups;
n is an integer from 0-to-40;
m is an integer from 1 to the total number of —OH hydrogens in the R group prior to alkoxylation;
p is an integer such that the sum of m plus p equals the number of —OH hydrogens in the R group prior to alkoxylation;
B is $SO_3Y$, $(CH_2)_q SO_3Y$, $CH_2CHOHCH_2SO_3Y$, or $CH_2CH(CH_3)OSO_3Y$,
where q is an integer from 2-to-4, and Y is a cation; and
R is compound selected from:

$$R^1 C(CH_2O)_3 \quad (II),$$

where $R^1$ is H, methyl, ethyl, or propyl;

$$C(CH_2O)_4 \quad (III);$$

$$OC(CH_2O)_2 \quad (IV);$$

$$N(CH_2CH_2O)_3 \quad (V);$$

$$(R^2)_x N(CH_2CH_2O)_y \quad (VI),$$

where $R^2$ is a $C_1$-$C_4$ alkyl, y is a number from 1-to-3, and x is a number such that x+y=3;

$$O(CH_2)_r O \quad (VII),$$

where r is a number from 2-to-6; and $$O(CH(CH_3)CH_2)O \quad (VIII);$$

$R^3$ is a group selected from:

$$C_6\text{-}C_{10}\text{-alkyl} \quad (X); \text{ and}$$

$$R^5 C(O)NH(CH_2)_z \quad (XI),$$

where $R^5$ is a $C_1$-$C_6$-alkyl, and z is 2 or 3; and
$R^4$ is a group selected from:

$$CH_2CO_2^- \quad (XII); \text{ and}$$

$$CH_2CH(R^6)CH_2SO_3^- \quad (XIII),$$

where $R^6$ is either H or OH.

2. The method according to claim 1, wherein said mist-suppressing quantity is in the range of from about 2-to-about 100 ppm.

3. The method according to claim 1, wherein, in the compounds of Formula (IX), $R^3$ represents $C_6$-$C_{12}$-alkyl; and $R^4$ represents $CH_2CO_2^-$.

4. The method according to claim 3, wherein $R^3$ is octyl, an octyl/decyl mixture, or decyl; and $R^4$ represents $CH_2CO_2^-$.

5. The method according to claim 4, wherein $R^3$ is decyl.

* * * * *